(12) United States Patent
Dirkzwager et al.

(10) Patent No.: US 7,282,474 B2
(45) Date of Patent: Oct. 16, 2007

(54) PROCESS FOR THE PREPARATION OF DETERGENTS

(75) Inventors: Hendrik Dirkzwager, Amsterdam (NL); Joannes Ignatius Geijsel, The Hague (NL)

(73) Assignee: Shell Oil Company, Houston, TX (US)

( * ) Notice: Subject to any disclaimer, the term of this patent is extended or adjusted under 35 U.S.C. 154(b) by 228 days.

(21) Appl. No.: 10/541,169

(22) PCT Filed: Dec. 29, 2003

(86) PCT No.: PCT/EP03/51106

§ 371 (c)(1),
(2), (4) Date: Jun. 30, 2005

(87) PCT Pub. No.: WO2004/058921

PCT Pub. Date: Jul. 15, 2004

(65) Prior Publication Data

US 2006/0189504 A1    Aug. 24, 2006

(30) Foreign Application Priority Data

Dec. 30, 2002   (EP) .................................. 02259016

(51) Int. Cl.
*C11D 17/00* (2006.01)
*C07C 27/00* (2006.01)
*C07C 1/00* (2006.01)

(52) U.S. Cl. .................. 510/357; 518/700; 585/323

(58) Field of Classification Search ................ 518/700; 510/357; 585/323

See application file for complete search history.

(56) References Cited

U.S. PATENT DOCUMENTS 3,239,455 A    3/1966  Lickus et al. ............... 208/212
3,674,885 A    7/1972  Griesinger et al. ...... 260/671 B
6,392,109 B1   5/2002  O'Rear et al. ............... 585/323
2002/0128530 A1  9/2002  Miller et al. ................ 585/517

FOREIGN PATENT DOCUMENTS

| AU | 698392 | 10/1998 |
| GB | 990744 | 4/1965 |
| WO | 99/34917 | 7/1999 |

OTHER PUBLICATIONS

International Search Report dated May 10, 2004.
Detergent Manufacture Including Zeolite Builders and Other New Materials, Ed. Sittig, Noyes Data Corp., NJ 1979.

*Primary Examiner*—J. Parsa

(57) ABSTRACT

A process for the preparation of detergents involving separating the hydrocarbonaceous product stream from a Fischer-Tropsch process producing normally liquid and normally solid hydrocarbons into a light fraction and one or more heavy fractions, hydrogenating at least part of the light fraction to convert unsaturated hydrocarbons and/or oxygenates into saturated hydrocarbons, distilling product thus obtained into at least one fraction comprising detergent hydrocarbons, dehydrogenating at least part of the detergent hydrocarbons to obtain a detergent hydrocarbon stream having mono-olefins and converting the mono-olefins into detergents. The invention further concerns a process for the preparation of detergents in which process a hydrogenated product, which is obtained according to the above process, is dehydrogenated to obtain a detergent hydrocarbon stream of mono-olefins, followed by conversion of the mono-olefins into detergents. Further, the invention relates to the combined production of detergents or detergent hydrocarbons and fuels from Fischer-Tropsch hydrocarbonaceous reaction product.

19 Claims, No Drawings

PROCESS FOR THE PREPARATION OF DETERGENTS

The present application claims priority to European Patent Application 02259016.0 filed 30 Dec. 2002.

FIELD OF THE INVENTION

BACKGROUND OF THE INVENTION

The present invention relates to a process for the preparation of detergents from hydrocarbonaceous Fischer-Tropsch product streams, especially Fischer-Tropsch product streams producing high amounts of normally liquid and especially normal solid hydrocarbons. The process more in particular concerns the preparation of detergents derived from linear or almost linear alkanes obtainable from the Fischer-Tropsch process and comprising 9 to 18 carbon atoms, preferably 10 to 17 carbon atoms, more preferably 10 to 13 carbon atoms. The invention further relates to the production of detergents or detergent hydrocarbons and fuels from hydrocarbonaceous Fischer-Tropsch products streams.

The preparation of detergents, especially biodegradable detergents, from linear olefins prepared in a Fischer-Tropsch process has been described in the literature. For instance, in ACS Symp. Series No. 238, 18-33 (191 ACS Nat. Meeting Div. Pet. Chem. Symp. New York, 13-18 Apr. 1986) it has been described that $C_9$-$C_{15}$ cuts of low and high temperature Fischer-Tropsch processes are suitable feedstocks in the alkylation of benzene to prepare alkylbenzenes, followed by sulfonation to convert the alkylbenzenes into alkylbenzene sulfonates. The direct products of these Fischer-Tropsch processes, using iron based catalysts, comprise rather large amounts of olefins and oxygenates (usually alcohols). For instance, the high temperature process results in a product comprising about 70% olefins (60% straight chain product), the low temperature process results in about 25% olefins (linearity 93%). Also, U.S. Pat. No. 3,674,885 describes the use of paraffin-olefin mixtures synthesized in a Fischer-Tropsch process in the alkylation of benzene. The paraffins are separated from the alkylation mixture and are recycled to a chlorination unit from which the paraffin-chloroparaffin effluent mixture is combined with the fresh Fischer-Tropsch olefin-paraffin mixture and the combined feeds are used to alkylate the benzene.

In the prior art processes, however, the separation and the use of the available detergent hydrocarbons is not optimal. Further, the presence of unsaturated compounds make storage and transport difficult. Additionally, the use of a chlorination process is undesirable.

SUMMARY OF THE INVENTION

The present invention is directed to a process for the preparation of detergents, comprising separating the hydrocarbonaceous product stream from a Fischer-Tropsch process producing normally liquid and normally solid hydrocarbons into a light fraction comprising mainly $C_{20}$-hydrocarbons, preferably at least 90% wt, more preferably at least 95% wt, of $C_{20}$-hydrocarbons, and one or more heavy fractions comprising the remaining hydrocarbons, hydrogenating at least part of the light fraction to convert unsaturated hydrocarbons and/or oxygenates into saturated hydrocarbons, distilling product thus obtained into at least one fraction comprising detergent hydrocarbons, dehydrogenating at least part of the detergent hydrocarbons to obtain a detergent hydrocarbon stream comprising mono-olefins and converting the mono-olefins into detergents.

In another embodiment, the invention is directed to a process for the preparation of detergents in which process a hydrogenated product, which product is obtained by separating the hydrocarbonaceous product stream from a Fischer-Tropsch process producing normally liquid and normally solid hydrocarbons into a light fraction comprising mainly $C_{20}$-hydrocarbons, preferably comprising at least 90% wt, more preferably at least 95% wt, of $C_{20}$-hydrocarbons, and one or more heavy fractions comprising the remaining hydrocarbons, hydrogenating at least part of the light fraction to convert unsaturated hydrocarbons and/or oxygenates into saturated hydrocarbons and distilling product thus obtained into at least one fraction comprising detergent hydrocarbons, is dehydrogenated to obtain a detergent hydrocarbon stream comprising mono-olefins, followed by conversion of the mono-olefins into detergents.

DETAILED DESCRIPTION OF THE INVENTION

In this specification the term "mainly" means at least 80% wt, unless otherwise specified. When an amount of a product or mixture is indicated as "% wt", the percentage is based on the total product stream in which the product is present, unless otherwise specified. By "normally liquid hydrocarbon product" is meant any product which is at STP (1 bar, 0° C.) a liquid product. For saturated hydrocarbons this means $C_{5+}$ hydrocarbons. By "normally solid product" is meant any product which is solid at STP. For saturated normal hydrocarbons this means $C_{15+}$. The term Cn+ relates to molecules comprising n carbon atoms or more. The term Cn− refers to molecules comprising n carbon atoms or less. The term "middle distillates", as used herein, is a reference to hydrocarbon mixtures of which the boiling point range corresponds substantially to that of kerosene and diesel fractions obtained in a conventional atmospheric distillation of crude mineral oil.

The present invention involves isolating a particular fraction from a Fischer-Tropsch product, followed by hydrogenation and distillation to obtain the desired detergent hydrocarbons (i.e. hydrocarbons to be used for the preparation of detergents, often $C_{10}$-$C_{13}$ and/or $C_{14}$-$C_{17}$ linear paraffins), followed by dehydrogenation to obtain a detergent hydrocarbon stream comprising mono-olefins and converting the mono-olefins into detergents using processes known in the art, these processes usually resulting in a mixture comprising between 5 and 20% mono-olefins. The proposed scheme has the advantage that very narrow production ranges can be obtained, as the distillation of hydrogenated product results in a more uniform carbon distribution pattern than a raw Fischer-Tropsch product comprising olefins and oxygenates (mainly alcohols). In addition, an optimum yield is obtained as none of the molecules having the desired number of carbon atoms ends up in the lower or higher boiling fraction. This is an important aspect, as, due to the tendency to maximize the carbon chain length of the products in the Fischer-Tropsch process, the amount of relatively low boiling compounds becomes less and less. Thus, an optimum use of the relatively low boiling products is desired. Further, such hydrogenated products are more stable and less corrosive than non-treated products, making transport and storage easier. In addition, the use of only a light fraction of the raw Fischer-Tropsch products avoids the need to hydrogenate the full Fischer-Tropsch fraction, as it is often not necessary to hydrogenate the heavy Fischer-Tropsch product.

The light Fischer-Tropsch fraction suitably comprises at least 80% wt (on total fraction) of $C_{20}$-products. Preferably the light fraction comprises 90% wt, more preferably 95% wt, $C_{18}$-hydrocarbons, especially at least 80% wt, preferably 90% wt, more preferably 95% wt, $C_{16}$-hydrocarbons, more especially at least 80% wt, preferably 90% wt, more preferably 95% wt, $C_{14}$-hydrocarbons. The light fraction comprises for a large part saturated paraffins, together with olefins and oxygenates. The oxygenates are mainly alcohols. The carbon skeleton of the paraffins, olefins and alcohols are identical, and usually contain between 2 and 20% wt, more usually between 4 and 14% wt, of branched carbon chains. The amount of branched structures depends on the actual process conditions (especially pressure, temperature, $H_2/CO$ ratio, catalyst, catalyst activators). Methyl groups, usually present in up to 15% of the molecules based on total molecules, more usually in up to 10%, are the main form of branches present.

Very suitably, the hydrocarbonaceous product stream of the Fischer-Tropsch process, before separation into the light fraction and the heavy fraction, is separated into a light stream, comprising most, suitably at least 80% wt, preferably 90% wt, more preferably 95% wt, of the $C_1$-$C_4$ hydrocarbons produced in the Fischer-Tropsch process, especially the light product stream comprising most, suitably at least 80% wt, preferably 90% wt, more preferably 95% wt, of the $C_1$-$C_3$ hydrocarbons produced in the Fischer-Tropsch process, and optionally unconverted synthesis gas constituents, carbon dioxide and other inert gases, and a heavy stream which is separated into the light and the heavy fraction. If still present, Fischer-Tropsch process water is also removed. In another embodiment the Fischer-Tropsch product stream is first separated into a light and a heavy fraction, followed by removal of the above described light stream.

In a further preferred embodiment, a light product is removed from the hydrocarbonaceous product stream from the Fischer-Tropsch process or the light stream as described above, the light product stream comprising mainly, especially at least 80% wt, the $C_7$-products, preferably the $C_8$-products, more preferably the $C_9$-products, present in the stream, especially the light product comprising at least 90% wt, more preferably at least 95% wt, of the $C_7$-products present, more especially the light product comprising at least 90% wt, preferably at least 95% wt, of the $C_8$-products present, still more especially the light product comprising at least 90% wt, more preferably at least 95% wt, of the $C_9$-products present.

In a preferred embodiment, resulting in an optimal and efficient use of the detergent hydrocarbons, the light fraction which is to be hydrogenated comprises mainly $C_9$- to $C_{18}$-hydrocarbons, preferably at least 80% wt $C_9$- to $C_{18}$-hydrocarbons, more preferably at least 90% wt, especially the light fraction comprising mainly $C_{10}$- to $C_{14}$-hydrocarbons, preferably at least 80% wt $C_{10}$ to $C_{13}$-hydrocarbons, more preferably at least 90% wt. In another preferred embodiment, the light fraction which is to be hydrogenated comprises at least 80% wt $C_{14}$- to $C_{18}$-hydrocarbons, preferably at least 90% wt, especially at least 80% wt $C_{14}$- to $C_{17}$-hydrocarbons, preferably at least 90% wt. In the above preferred embodiment, the distillation of the hydrogenated hydrocarbons is not always necessary, and thus is an optimal feature. The boiling range is suitably between 160° C. and 330° C., preferably between 170° C. and 320° C. Especially preferred are the ranges between 170° C. and 240° C. and between 250° C. and 310° C.

The Fischer-Tropsch process is suitably a low temperature process. In the Fischer-Tropsch process a mixture of hydrogen and carbon monoxide is catalytically converted into hydrocarbons and water. The Fischer-Tropsch catalysts are known in the art. Catalysts for use in this process frequently comprise, as the catalytically active component, a metal from Group VIII of the Periodic Table of Elements. Particular catalytically active metals include ruthenium, iron, cobalt and nickel. Cobalt is a preferred catalytically active metal in view of the heavy Fischer-Tropsch hydrocarbon which can be made. Preferred hydrocarbonaceous feeds are natural gas or associated gas. As these feedstocks usually result in synthesis gas having $H_2/CO$ ratio's of about 2, cobalt is a very good Fischer-Tropsch catalyst as the user ratio for this type of catalysts is also about 2.

The catalytically active metal is preferably supported on a porous carrier. The porous carrier may be selected from any of the suitable refractory metal oxides or silicates or combinations thereof known in the art. Particular examples of preferred porous carriers include silica, alumina, titania, zirconia, ceria, gallia and mixtures thereof, especially silica, alumina and titania.

The amount of catalytically active metal on the carrier is preferably in the range of from 3 to 300 pbw per 100 pbw of carrier material, more preferably from 10 to 80 pbw, especially from 20 to 60 pbw.

If desired, the catalyst may also comprise one or more metals or metal oxides as promoters. Suitable metal oxide promoters may be selected from Groups IIA, IIIB, IVB, VB and VIB of the Periodic Table of Elements, or the actinides and lanthanides. In particular, oxides of magnesium, calcium, strontium, barium, scandium, yttrium, lanthanum, cerium, titanium, zirconium, hafnium, thorium, uranium, vanadium, chromium and manganese are very suitable promoters. Particularly preferred metal oxide promoters for the catalyst used to prepare the waxes for use in the present invention are manganese and zirconium oxide. Suitable metal promoters may be selected from Groups VIIB or VIII of the Periodic Table. Rhenium and Group VIII noble metals are particularly suitable, with platinum and palladium being especially preferred. The amount of promoter present in the catalyst is suitably in the range of from 0.01 to 100 pbw, preferably 0.1 to 40, more preferably 1 to 20 pbw, per 100 pbw of carrier. The most preferred promoters are selected from vanadium, manganese, rhenium, zirconium and platinum.

The catalytically active metal and the promoter, if present, may be deposited on the carrier material by any suitable treatment, such as impregnation, kneading and extrusion. After deposition of the metal and, if appropriate, the promoter on the carrier material, the loaded carrier is typically subjected to calcination. The effect of the calcination treatment is to remove crystal water, to decompose volatile decomposition products and to convert organic and inorganic compounds to their respective oxides. After calcination, the resulting catalyst may be activated by contacting the catalyst with hydrogen or a hydrogen-containing gas, typically at temperatures of about 200 to 350° C. Other processes for the preparation of Fischer-Tropsch catalysts comprise kneading/mulling, often followed by extrusion, drying/calcination and activation.

The catalytic conversion process may be performed under conventional synthesis conditions known in the art. Typically, the catalytic conversion may be effected at a temperature in the range of from 180 to 270° C., preferably from 200 to 250° C. Typical total pressures for the catalytic conversion process are in the range of from 10 to 100 bar absolute, more preferably from 20 to 65 bar absolute. In the catalytic conversion process preferably more than 75% wt of $C_{5+}$, and more preferably more than 85% wt $C_{5+}$ hydrocarbons are formed. Depending on the catalyst and the conversion conditions, the amount of heavy wax ($C_{20+}$) may be up to 60% wt, sometimes up to 70% wt, and sometimes up to 85% wt. Preferably a cobalt catalyst is used, a low $H_2/CO$ ratio is used (especially 1.7, or even lower) and a low temperature is used (190-240° C.), optionally in combination with a high pressure. To avoid any coke formation, it is preferred to use an $H_2/CO$ ratio of at least 0.3. It is especially preferred to carry out the Fischer-Tropsch reaction under such conditions that the ASF-alpha value (Anderson-Schulz-Flory chain growth factor), for the obtained products having at least 20 carbon atoms, is at least 0.925, preferably at least 0.935, more preferably at least 0.945, even more preferably at least 0.955. Preferably the Fischer-Tropsch hydrocarbons stream comprises at least 40% wt $C_{30+}$, preferably 50% wt, more preferably 55% wt, and the weight ratio $C_{60+}/C_{30+}$ is at least 0.35, preferably 0.45, more preferably 0.55.

A most suitable catalyst for this purpose is a cobalt-containing Fischer-Tropsch catalyst. Such catalysts are described in the literature, see e.g. AU 698392 and WO 99/34917.

The Fischer-Tropsch process may be a slurry FT process or a fixed bed FT process, especially a multitubular fixed bed.

The separation of the product stream of the Fischer-Tropsch process into a light and a heavy fraction, as well the other separations, is carried out by distillation, preferably at ambient pressure. Commercially available equipment may be used. The separation of the light stream comprising mainly gaseous compounds at STP, may be done in a gas/liquid separation step.

In the hydrogenation step in the process of the present invention, the light fraction is contacted with hydrogen in the presence of a hydrogenation catalyst. Suitable catalysts for use in this stage are known in the art. Typically, the catalyst comprises as catalytically active component one or more metals selected from Groups VIB and VIII of the Periodic Table of Elements, in particular one or more metals selected from molybdenum, tungsten, cobalt, nickel, ruthenium, iridium, osmium, platinum and palladium. Preferably, the catalyst comprises on or more metals selected from nickel, platinum and palladium as the catalytically active component.

A particularly suitable catalyst comprises nickel as a catalytically active component.

Catalysts for use in the hydrogenation step typically comprise a refractory metal oxide or silicate as a carrier. Suitable carrier materials include silica, alumina, silica-alumina, zirconia, titania and mixtures thereof. Preferred carrier materials for inclusion in the catalyst for use in the process of this invention are silica, alumina and silica-alumina.

The catalyst may comprise the catalytically active component in an amount of from 0.05 to 80 parts by weight, preferably from 0.1 to 70 parts by weight, per 100 parts by weight of carrier material. The amount of catalytically active metal present in the catalyst will vary according to the specific metal concerned. One particularly suitable catalyst for use in the first hydroconversion stage comprises nickel in an amount in the range of from 30 to 70 parts by weight per 100 parts by weight of carrier material. A second particularly suitable catalyst comprises platinum in an amount in the range of from 0.05 to 2.0 parts by weight per 100 parts by weight of carrier material.

Suitable catalysts for use in the hydrogenation step of the process of this invention are available commercially, or may be prepared by methods well known in the art, for example the methods discussed hereinbefore with reference to the preparation of the hydrocarbon synthesis catalyst.

In the hydrogenation step, the hydrocarbon product is contacted with hydrogen at elevated temperature and pressure. The operating temperature may typically range from 100 to 300° C., more preferably from 150 to 275° C., in particular from 175 to 250° C. Typically, the operating pressure ranges from 5 to 150 bars, preferably from 10 to 50 bars. Hydrogen may be supplied to the hydroconversion stage at a gas hourly space velocity in the range of from 100 to 10000 Nl/l/hr, more preferably from 250 to 5000 Nl/l/hr. The hydrocarbon product being treated is typically supplied to the hydroconversion stage at a weight hourly space velocity in the range of from 0.1 to 5 kg/l/hr, more preferably from 0.25 to 2.5 kg/l/hr. The ratio of hydrogen to hydrocarbon product may range from 100 to 5000 Nl/kg and is preferably from 250 to 3000 Nl/kg.

The hydrogenation step is operated under conditions such that substantially isomerization or hydrocracking of the feed occurs. The precise operating conditions required to achieve the desired degree of hydrogenation without substantial hydrocracking or hydroisomerization occurring will vary according to the composition of the hydrocarbon product being fed to the hydroconversion stage and the particular catalyst being employed. As a measure of the severity of the conditions prevailing in the first hydroconversion stage and, hence, the degree of hydrocracking and isomerization occurring, the degree of conversion of the feed hydrocarbon may be determined. In this respect, conversion, in percent, is defined as the percent weight of the fraction of the feed boiling above 220° C. which is converted during the hydroconversion to a fraction boiling below 220° C. The conversion of the first hydroconversion stage is below 20%, preferably below 10%, more preferably below 5%. In the case that there is too much hydroisomerization and/or hydrocracking a decrease of the temperature may resolve the problem.

After the hydrogenation step the resulting product is distilled in such a way that the desired detergent hydrocarbons are obtained. Commercially available equipment may be used. The distillation may be carried out at atmospheric pressure, but reduced pressure may also be used.

The desired detergent hydrocarbons are then dehydrogenated. This may be done using processes well known in the art. For instance, the PACOL process of UOP optionally complemented by the DEFINE process of UOP (to convert any dienes in the feed to mono-olefins).

In general, dehydrogenation of the detergent hydrocarbons in the instant process may be accomplished using any of the well-known dehydrogenation catalyst systems "conventional dehydrogenation catalysts" including those described in "Detergent Manufacture Including Zeolite Builders and Other New Materials", Ed. Sittig, Noyes Data Corp., New Jersey, 1979 and other dehydrogenation catalyst systems, for example those commercially available though UOP Corp. Dehydrogenation may be conducted in the presence of hydrogen gas and a precious metal catalyst though alternatively non-hydrogen, precious-metal free dehydrogenation systems such as a zeolite/air system may be used.

Dehydrogenation may be complete or partial, more typically partial. Usually between 5 and 50% wt olefins are formed, suitably between 5 and 20% wt. When partial, this step forms a mixture of olefin and unreacted paraffin. Such mixture may be a suitable feed for a benzene alkylation step.

After work up of an alkylation step, the unconverted paraffins may be recirculated to the start of the dehydrogenation process.

Suitably the dehydrogenation process uses a catalyst containing molybdenum, tungsten, cobalt, nickel, ruthenium, iridium, osmium, platinum or palladium as a catalytically active metal, preferably one or more of nickel and/or molybdenum, cobalt and/or tungsten, platinum and palladium, more preferably platinum.

The dehydrogenation step is suitably carried out at a temperature between 300 and 600° C., preferably between 400 and 500° C., a pressure between 1 and 20 bar, preferably between 1 and 4 bar.

Following the dehydrogenation, the detergent hydrocarbon is converted into a detergent according to methods well known in the art. Suitably, the reaction is selected from the following reactions:
- alkylation with benzene or toluene optionally followed by sulfonation and neutralization;
- alkylation with phenol followed by at least one of alkoxylation, sulfonation and neutralization, sulfation and neutralization or alkoxylation combined with oxidation;
- hydroformylation optionally followed by at least one of alkoxylation, glycosylation, sulfation, phosphatization or combinations thereof
- sulfonation;
- epoxidation;
- hydrobromination followed by amination and oxidation to amine oxide; and
- phosphonation.

A particularly preferred option is the alkylation of monoaromatic compounds, e.g. benzene, toluene, xylene and mixtures thereof, followed by sulfonation The alkylation process may use aluminium chloride, hydrogen fluoride, fluoridated zeolites, non-acidic calcium mordenite and the like as catalyst. For example, appropriate process conditions for ALC13 alkylation are exemplified by a reaction of 5 mole % ALC13 relative to the detergent hydrocarbon at 100-300° C. for 0.5-1.0 hour in a batch or continuous reactor. Other suitable alkylation catalyst may be selected from shape-selective moderately acidic alkylation catalysts, preferably zeolitic. The zeolite in such catalysts for the alkylation step is preferably selected from the group consisting of mordenite, ZSM-4, ZSM-12, ZSM-20, offretite, gmelinite and zeolite beta in at least partially acidic form. More preferably, the zeolite in the alkylation step is substantially in acid form and is contained in a catalyst pellet comprising a conventional binder and further wherein said catalyst pellet comprises at least about 1%, more preferably at least 5%, more typically from 50% to about 90%, of said zeolite.

More generally, a suitable alkylation catalyst is typically at least partially crystalline, more preferably substantially crystalline not including binders or other materials used to form catalyst pellets, aggregates or composites. Moreover, the catalyst is typically at least partially acidic. H-form mordenite is an example of a suitable catalyst.

The pores characterizing the zeolites useful in the present alkylation process may be substantially circular, such as in canchinite which has uniform pores of about 6.2 Angstroms, or preferably may be somewhat elliptical, such as in mordenite. The zeolites used as catalysts in the alkylation step of the present process may have a major pore dimension intermediate between that of the large pore zeolites, such as the X and Y zeolites, and the relatively small pore size zeolites ZSM-5 and ZSM-11, preferably between about 6 Angstroms and about 7 Angstroms. The pore size dimensions and crystal structures of certain zeolites are specified in ATLAS OF ZEOLITE STRUCTURE TYPES by W. M. Meier and D. H. Olson, published by the Structure Commission of the International Zeolite Association (1978 and more recent editions). The zeolites may be subjected to various chemical treatments, including alumina extraction (dealumination) and combination with one or more metal components, particularly the metals of Groups IIB, III, IV, VI, VII and VIII. It is also contemplated that the zeolites may, in some instances, desirably be subjected to thermal treatment, including steaming or calcination in air, hydrogen or an inert gas, e.g. nitrogen or helium. In practicing the desired alkylation step of the instant process, it may be useful to incorporate the above-described intermediate pore size crystalline zeolites in another material, e.g., a binder or matrix resistant to the temperature and other conditions employed in the process. Such matrix materials include synthetic or naturally occurring substances as well as inorganic materials such as clay, silica, and/or metal oxides. Matrix materials may be in the form of gels including mixtures of silica and metal oxides.

The process of the invention is also directed to a process for the preparation of detergents and hydrocarbon fuels from the product stream of a Fischer-Tropsch process, comprising a process as described above for the preparation of detergents from a light fraction of the Fischer-Tropsch process in combination with the hydrocracking/hydroisomerization of the one or more heavy fractions of the Fischer-Tropsch process.

In the hydrocracking/hydroisomerization step, hydrocarbon fuels are prepared from the hydrocarbon product of the one or more heavy Fischer-Tropsch fractions by hydrocracking and hydroisomerizing the product with hydrogen in the presence of a suitable catalyst. Typically, the catalyst comprises as catalytically active component one or more metals selected from Groups VIB and VIII of the Periodic Table of Elements, in particular one or more metals selected from molybdenum, tungsten, cobalt, nickel, ruthenium, iridium, osmium, platinum and palladium. Preferably, the catalyst comprises one or more metals selected from nickel, platinum and palladium as the catalytically active component. Catalysts comprising platinum as the catalytically active component have been found to be particularly suitable for use in the second hydroconversion stage.

Catalysts for use in the second hydroconversion stage typically comprise a refractory metal oxide or silicate as a carrier. The carrier material may be amorphous or crystalline. Suitable carrier materials include silica, alumina, silica-alumina, zirconia, titania and mixtures thereof. The carrier may comprise one or more zeolites, either alone or in combination with one or more of the aforementioned carrier materials. Preferred carrier materials for inclusion in the catalyst for use in the process of this invention are silica, alumina and silica-alumina. A particularly preferred catalyst comprises platinum supported on a silica-alumina carrier.

The catalyst may comprise the catalytically active component in an amount of from 0.05 to 80 parts by weight, preferably from 0.1 to 70 parts by weight, per 100 parts by weight of carrier material. The amount of catalytically active metal present in the catalyst will vary according to the specific metal concerned. A particularly preferred catalyst for use in the second hydroconversion stage comprises platinum in an amount in the range of from 0.05 to 2 parts by weight, more preferably from 0.1 to 1 parts by weight, per 100 parts by weight of carrier material.

Suitable catalysts for use in the hydrocracking/hydroisomerization stage of the process of this invention are available commercially, or may be prepared by methods well known in the art, for example the methods discussed hereinbefore with reference to the preparation of the hydrocarbon synthesis catalyst.

In the hydrocracking/hydroisomerization stage of this process, the heavy Fischer-Tropsch hydrocarbon product is contacted with hydrogen in the presence of the catalyst at elevated temperature and pressure. Typically, the temperatures necessary to yield the hydrocarbon fuels will lie in the range of from 200 to 400° C., preferably from 275 to 375° C. The pressure typically applied ranges from 20 to 250 bars, more preferably from 40 to 200 bars. Hydrogen may be supplied at a gas hourly space velocity of from 100 to 10000 Nl/l/hr, preferably from 500 to 5000 Nl/l/hr. The hydrocarbon feed may be provided at a weight hourly space velocity of from 0.1 to 5 kg/l/hr, preferably from 0.25 to 2 kg/l/hr. The ratio of hydrogen to hydrocarbon feed may range from 100 to 5000 Nl/kg and is preferably from 250 to 2500 Nl/kg.

As discussed hereinbefore, the degree of hydrocracking and isomerisation occurring in the hydrocracking/hydroisomerization stage may be measured by determining the degree of conversion of the fraction boiling above 370° C. Typically, the hydrocracking/hydroisomerization stage is operated at a conversion of at least 40%.

The hydrogen required for the operation of the two hydroconversion stages may be generated by processes well known in the art, for example by the steam reforming of a refinery fuel gas.

The hydrocarbon fuel produced in the second hydroconversion stage will typically comprise hydrocarbons having boiling points lying in a number of ranges for different fuel fractions, for example naphtha, kerosene and gasoil fractions. Separation of the hydrocarbon fuel into the appropriate fractions may be conveniently achieved using distillation techniques well known in the art.

In the process of the invention any reject streams obtained in the above described distillation processes may very suitably be used as additional feedstreams in the process for the preparation of fuels.

The present invention is further directed to a process for the preparation of detergent hydrocarbons comprising separating the hydrocarbonaceous product stream of a Fischer-Tropsch process producing normally liquid and normally solid hydrocarbons into a light fraction comprising mainly $C_{20}$-hydrocarbons, preferably $C_{18}$-, more preferably $C_{16}$-, still more preferably $C_{14}$-hydrocarbons, and one or more heavy fractions comprising the remaining hydrocarbons, hydrogenation of the light fraction to convert unsaturated hydrocarbons and/or oxygenates into saturated hydrocarbons, distillation of product thus obtained into at least one fraction comprising detergent hydrocarbons and optionally dehydrogenation of at least part of the detergent hydrocarbons to obtain a detergent hydrocarbon stream comprising mono-olefins. Preferably the process comprises the use of any one or more reject streams, e.g. obtained in the distillation processes, in the process for the preparation of detergent hydrocarbons as additional feedstreams in the process for the preparation of fuels. A preferred range of $C_{14}$-$C_{17}$ detergent hydrocarbons may be converted into detergents via chlorination or sulfonation of the hydrogenated $C_{14}$-$C_{17}$ stream.

The invention is further directed to a process for the preparation of detergent hydrocarbons and hydrocarbon fuels from the product stream of a Fischer-Tropsch process, comprising a process as described above for the preparation of detergent hydrocarbons from a light fraction of the Fischer-Tropsch process in combination with the hydrocracking/hydroisomerization of the heavy product stream of the Fischer-Tropsch process.

The invention is further directed to a process for the preparation of detergents comprising dehydrogenation of detergent hydrocarbons to obtain a detergent hydrocarbon stream comprising mono-olefins and conversion of the mono-olefins into detergents, the detergent hydrocarbons being prepared by separating the product stream of a Fischer-Tropsch process into a light fraction comprising mainly $C_{20}$-hydrocarbons, preferably $C_{18}$-, more preferably $C_{16}$-, still more preferably $C_{14}$-hydrocarbons, and a heavy fraction comprising the remaining hydrocarbons, hydrogenation of the light fraction to convert unsaturated hydrocarbons and/or oxygenates into saturated hydrocarbons, distillation of product thus obtained into at least one fraction comprising detergent hydrocarbons.

We claim:

1. A process for the preparation of detergents, comprising separating a hydrocarbonaceous product stream from a Fischer-Tropsch process producing normally liquid and normally solid hydrocarbons into a light fraction comprising mainly $C_{18-}$ hydrocarbons and one or more heavy fractions comprising the remaining hydrocarbons;
   hydrogenating at least part of the light fraction to convert unsaturated hydrocarbons and/or oxygenates into saturated hydrocarbons;
   distilling product thus obtained into at least one fraction comprising $C_{10}$-$C_{17}$ detergent hydrocarbons;
   dehydrogenating at least part of the detergent hydrocarbons to obtain a detergent hydrocarbon stream comprising mono-olefins; and,
   converting the mono-olefins into detergents.

2. The process of claim 1, in which the light fraction comprises mainly $C_{16-}$ hydrocarbons.

3. The process of claim 1, further comprising separating the hydrocarbonaceous product stream of the Fischer-Tropsch process into a light stream, comprising at least 80 wt % of $C_1$-$C_4$ hydrocarbons produced in the Fischer-Tropsch process and optionally unconverted synthesis gas constituents, carbon dioxide and other inert gasses, and a heavy stream which is separated into the light fraction and the heavy fraction.

4. The process of claim 1, further comprising removing a light product stream from the hydrocarbonaceous product stream from the Fischer-Tropsch process or the light stream, wherein the light product stream comprises mainly $C_{7-}$ products present in the stream.

5. The process of claim 1, in which the light fraction comprises at least 80 wt % $C_9$- to $C_{18-}$ hydrocarbons.

6. The process of claim 1, in which converting the mono-olefins into detergents comprises at least one step selected from the group consisting of:
   alkylating with benzene or toluene optionally followed by sulfonating and neutralizing;
   alkylating with phenol followed by at least one step selected from the group consisting of alkoxylating, sulfonating and neutralizing, sulfating and neutralizing and alkoxylating combined with oxidizing;
   hydroformylating optionally followed by at least one step selected from the group consisting of alkoxylating, glycosylating, sulfating, phosphatizing and combinations thereof;
   sulfonating;
   epoxidizing;

hydrobrominating followed by aminating and oxidizing to amine oxide; and
phosphonizing.

7. The process of claim 1, further comprising hydrocracking/hydroisomerizing the one or more heavy fractions of the Fischer-Tropsch process.

8. A process for the preparation of detergent hydrocarbons comprising separating a hydrocarbonaceous product stream of a Fischer-Tropsch process producing normally liquid and normally solid hydrocarbons into a light fraction comprising mainly $C_{18-}$ hydrocarbons, and one or more heavy fractions comprising the remaining hydrocarbons, hydrogenating the light fraction to convert unsaturated hydrocarbons and/or oxygenates into saturated hydrocarbons, distilling product thus obtained into at least one fraction comprising $C_{10}$-$C_{17}$ detergent hydrocarbons and optionally one or more reject streams and optionally dehydrogenating at least part of the detergent hydrocarbons to obtain a detergent hydrocarbon stream comprising mono-olefins.

9. The process of claim 8, in which any one or more reject streams in the process for the preparation of detergent hydrocarbons are used as additional feedstreams in a process for preparation of fuels.

10. The process of claim 8, further comprising hydrocracking/hydroisomerizing the heavy product stream of the Fischer-Tropsch process.

11. A process for the preparation of detergents comprising dehydrogenating $C_{10}$-$C_{17}$ detergent hydrocarbons to obtain a detergent hydrocarbon stream comprising mono-olefins and converting the mono-olefins into detergents, wherein the detergent hydrocarbons are prepared by a process comprising separating the product stream of a Fischer-Tropsch process into a light fraction comprising mainly $C_{18-}$ hydrocarbons, and a heavy fraction comprising remaining hydrocarbons, hydrogenating the light fraction to convert unsaturated hydrocarbons and/or oxygenates into saturated hydrocarbons, and, distilling product thus obtained into at least one fraction comprising $C_{10}$-$C_{17}$ detergent hydrocarbons.

12. The process of claim 1, in which the light fraction comprises at least 90 wt % of $C_{18-}$ hydrocarbons.

13. The process of claim 1, in which the light fraction comprises at least 90 wt % of $C_{16-}$ hydrocarbons.

14. The process of claim 1, in which the light fraction comprises at least 90 wt % of $C_{14-}$ hydrocarbons.

15. The process of claim 3, in which the light stream comprises at least 80 wt % of $C_1$-$C_3$ hydrocarbons produced in the Fischer-Tropsch process.

16. The process of claim 4, in which the light product stream comprises at least 90 wt % of $C_{7-}$ products.

17. The process of claim 1, in which the light fraction comprises at least 80 wt % $C_{14}$ to $C_{17}$ hydrocarbons.

18. The process of claim 6, further comprising hydrocracking/hydroisomerizing the one or more heavy fractions of the Fischer-Tropch process.

19. The process of claim 18, in which the light fraction comprises at least 80 wt % $C_{14}$ to $C_{17}$ hydrocarbons.

* * * * *